(12) United States Patent
Berg et al.

(10) Patent No.: US 6,704,602 B2
(45) Date of Patent: Mar. 9, 2004

(54) IMPLANTED MEDICAL DEVICE/EXTERNAL MEDICAL INSTRUMENT COMMUNICATION UTILIZING SURFACE ELECTRODES

(75) Inventors: Gary Berg, Edina, MN (US); Jill H. Ernst, Apple Valley, MN (US); Chester G. Nelson, Maple Grove, MN (US); Charles Stomberg, Forest Lake, MN (US); Jeffrey D. Wilkinson, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/423,101
(22) PCT Filed: Jul. 2, 1998
(86) PCT No.: PCT/US98/06103
§ 371 (c)(1),
(2), (4) Date: Oct. 29, 1999
(87) PCT Pub. No.: WO00/10641
PCT Pub. Date: Mar. 2, 2000

(65) Prior Publication Data
US 2002/0099423 A1 Jul. 25, 2002

(51) Int. Cl.[7] .............................................. A61N 1/362
(52) U.S. Cl. ........................................................ 607/60
(58) Field of Search ........................... 607/1, 2, 27, 29, 607/32, 59, 60; 600/510

(56) References Cited

U.S. PATENT DOCUMENTS

| | | |
|---|---|---|
| 3,946,744 A | 3/1976 | Auerbach |
| 4,151,513 A | 4/1979 | Menken et al. |
| 4,374,382 A | 2/1983 | Markowitz |
| 4,418,695 A | 12/1983 | Buffet |
| 4,522,208 A | 6/1985 | Buffet |
| 4,531,527 A | 7/1985 | Reinhold, Jr. et al. |
| 4,681,111 A * | 7/1987 | Silvain ......................... 607/59 |
| 4,702,253 A | 10/1987 | Nappholz et al. |
| 4,886,064 A | 12/1989 | Strandberg |
| 4,987,897 A * | 1/1991 | Funke ........................... 607/32 |
| 5,085,224 A | 2/1992 | Galen et al. |
| 5,113,869 A | 5/1992 | Nappholz et al. |
| 5,267,150 A | 11/1993 | Wilkinson |
| 5,300,093 A | 4/1994 | Koestner et al. |
| 5,304,209 A | 4/1994 | Adams et al. |
| 5,313,953 A | 5/1994 | Yomtov et al. |
| 5,404,877 A | 4/1995 | Nolan et al. |
| 5,411,535 A | 5/1995 | Fujii et al. |
| 5,413,593 A | 5/1995 | Spinelli et al. |
| 5,503,158 A | 4/1996 | Coppock et al. |
| 5,544,661 A | 8/1996 | Davis et al. |
| 5,549,654 A | 8/1996 | Powell |
| 5,549,659 A | 8/1996 | Johansen et al. |
| 5,556,421 A | 9/1996 | Prutichi et al. |
| 5,586,556 A | 12/1996 | Spivey et al. |
| 5,741,314 A * | 4/1998 | Daly et al. ..................... 607/60 |
| 5,899,928 A * | 5/1999 | Sholder et al. ................ 607/27 |
| 5,999,857 A * | 12/1999 | Weijland et al. .............. 607/60 |
| 6,141,592 A * | 10/2000 | Pauly ........................... 607/60 |

OTHER PUBLICATIONS

"Implantable Leads" Designation and Technical Data, Copyright 1985 by BIOTRONIK GmbH & Co.

"Thermos 02 Single Chamber Pacing with Physiological Temperature Controlled Rate Adaptation" Copyright 1990 BIOTRONIK GmbH & Co.

Schaldach, M., "Compensation of Chronotropic Incompetence with Temperature–Controlled Rate Adaptive Pacing", Biomed. Technik 33 (1988). 286–294.

* cited by examiner

Primary Examiner—George R. Evanisko
(74) Attorney, Agent, or Firm—Girma Wolde-Michael; Michael C. Soldner; Daniel G. Chapik (57) ABSTRACT

A medical device communications system uses subthreshold pulses, modulated to provide relatively high speed electrical communications with inexpensive external devices connectable to a body with the implant by surface leads.

3 Claims, 5 Drawing Sheets

IMPLANTED MEDICAL DEVICE/EXTERNAL MEDICAL INSTRUMENT COMMUNICATION UTILIZING SURFACE ELECTRODES

FIELD OF THE INVENTION

This invention is related to inter-device communications between medical devices and most particularly to systems that employ sub stimulation threshold pulses for such communications.

BACKGROUND

The high cost and general level of difficulty in communicating with an implanted medical device using a low cost external instrument has prevented widespread usage of the data which is currently available from pacemaker and other implantable medical devices to augment traditional transtelephonic home follow-up.

Health care systems are increasingly emphasizing and rewarding those products which reduce the cost of obtaining, communicating, and managing patient data. Therefore inexpensive devices for remotely monitoring the essential status of pacemaker patients and patients with other implantable medical devices is highly desirable. Even small improvements may have significant economic and medical benefit.

Difficulties arise in transferring large amounts of data between an implanted medical device and external monitors or other medical communications systems. Telemetry using RF or E fields and H fields is commonly practiced in, for example, the field of implantable devices such as pacemakers and defibrillator/cardioversion devices in communicating information between the implant and the external transceiving device for example, a programmer. This has limitations as well, primarily on the cost for the external device which goes up considerably if it needs to receive telemetry. Also, the energy cost of transmitting information from the implanted device to outside the patient's body is higher than using subthreshold electrical pulses and this therefore depletes the implant's battery, weighing against using telemetry too. The overriding consideration for employing external devices to receive data through skin contact electrodes is the simplicity and low cost of the one-way (receiving) device. (The receiving device could even be worn like a wrist watch and receive subthreshold communications for later retransmission).

Therefore to enable better device transmitted communications as the data amounts and transfer rates are desirably increased, a communications protocol and implementing hardware that facilitates such communications has been developed and is the subject of this document.

A list of references where similar or related inventions in the same or other unrelated fields were contemplated follows, and is incorporated into this disclosure by this reference thereto.

| | | |
|---|---|---|
| Davis et al. | U.S. Pat. No. | 5,544,661, |
| Spinelli et at. | U.S. Pat. No. | 5,413,593, |
| Coppock et al. | U.S. Pat. No. | 5,503,158, |
| Yomotov, et al. | U.S. Pat. No. | 5,313,953, |
| Fujii et al. | U.S. Pat. No. | 5,411,535, |
| Nappholz et al. | U.S. Pat. No. | 5,113,869, |
| Nolan et al. | U.S. Pat. No. | 5,404,877, |
| Prutchi et at. | U.S. Pat. No. | 5,556,421, |
| Funke | U.S. Pat. No. | 4,987,897, and |
| Strandberg | U.S. Pat. No. | 4,886,064. |

Additionally the Cardiac Telecom HEARTTrac(tm) cardiac monitoring system may provide additional information about such communications but at this date the inventors have not had an opportunity to review this matter.

There still is a need for a very inexpensive method of getting large amounts of data from an implanted device to an external device that is as yet unsatisfied by this art. This is especially true in rural areas and in places where sophisticated telemetry systems may be difficult to use or obtain.

SUMMARY OF THE INVENTION

In general this invention provides a way for an implantable medical device to communicate a limited amount of stored data or sensor or status data such as battery status and lead condition to an inexpensive external instrument. Additionally it would be an advantage to be able to also transmit marker data for electrocardiograms. Rather than relying on the more traditional telemetry communications channel which requires a large amount of support circuitry and so forth, we are using certain subthreshold electrical pulsing capability present in some current implantable medical devices for this purpose. This subthreshold pulsing may be delivered along different pathways for minute ventilation, lead impedance, and capture detection, as well as for this new communications purpose. In a preferred embodiment this circuit 10 outputs pulses at rates up to 125 Hz. By modulating a series of such pulses we can easily send data at 10 to 100 bps or even higher data rates. Preferably, communication occurs on a dedicated set of such pulses.

The pulse train can be by modulated to include data in several ways. The form (its amplitude or width for example) of the wave of the communications pulse may be varied in discrete steps. Including or omitting pulses at a given time in a segment length of time can represent various forms of data. Pairing of pulses to send a data bit may be employed. For example, a zero (0) bit could be represented by a pulse followed by a missing pulse, while a one (1) would be represented by a missing pulse followed by a pulse. By limiting ourselves to having at least one missing pulse every two pulse locations, we eliminate the possibility of a 00 or 11 configuration and enhance reliability in reading and allows for easier synchronization by this limitation too. Again, since it is so much less costly we make the communication be only one way. However, so that the implanted device is not communicating constantly to a turned off or disconnected receiver, it is also preferable to trigger a communications episode or session from external to the implanted device. This can be done with a simple "telemetry system" or a substitute for one like a magnet and an internal reed switch that is in the implant device circuitry and which when triggered by the presence of the magnet, begins a communications episode. (Of course, if a more sophisticated external device is used this sub threshold communication may run simultaneously with or be triggered by the H or E field telemetry. But the preferred embodiments will use simple triggers like sounds or magnets or externally applied electrical pulses, or a short burst of H or E field signal produced by an inexpensive external trigger device.) More specifically, each pulse is adapted to avoid pacing, or any tissue stimulation, and to avoid or minimize its effect on the lead to tissue interface. The size of the electrical pulse energy is therefore below the threshold required for cardiac or skeletal muscle stimulation. These pulses can be safely applied by a pacemaker electrode in a pattern which makes them easily and reliably detectable and interpretable by a simple external device.

A few modifications to currently known devices for delivering subthreshold pulses allows for delivery of modulated pulses. A simple detection algorithm can be implemented in external receivers which normally read electrograms of the patient by use of skin electrodes. The data read can be translated, error-checked, or otherwise modified to transmit the data to the external device. The external device can store this or transmit it to other devices or employ it directly to display diagnostically useful information or device related information for attending technicians or physicians.

In general then the invention is a communications system for communicating between an implanted medical device and a device external to a living body containing said implanted medical device wherein communications of data from within said implanted medical device to said external device is accomplished by a communications circuit for producing modulated biphasic subthreshold pulses in a pattern of modulations predetermined to represent data and insufficiently energetic to cause a physiologically significant reaction in living body tissue, and wherein said modulated pulses are transmitted across two electrodes electrically connected to said implanted device, said electrodes linkable in an electrical circuit from said communications circuit through tissues of said living body, such that said transmission can be received by an external device through a plurality of electrodes connected to said external device when such external device electrodes are in contact with the surface of said body, and the modulations of said subthreshold pulses will be at least one of the set of modulations comprising (adjustments to timing between delivery of pulses, changing amplitude of pulses, absence of a pulse or pulses in a train of pulses, altered or alternating polarity of pulses, and alterations in pulse width).

It has a medical information device for receiving modulated biphasic subthreshold electrical pulses in a pattern of modulations predetermined to represent data and insufficiently energetic to cause a physiologically significant reaction in living body tissue through electrodes for affixation to a living body surface having a detecting circuit for detecting said subthreshold pulses through said electrodes, comprising an amplifier circuit connected to said electrodes and producing an amplified output signal representing an electrical waveform composed substantially of said modulations of said pulses, and having a detecting circuit output for sending said amplified output signal, a decoding circuit comprising a circuit for reading each pulse modulation in said representation of the electrical waveform sent on said detecting circuit output, and for determining a data bit pattern representing data decoded from said modulations in said representation of said electrical waveform, and a conversion circuit for producing a signal representative of the useful information in said bit pattern.

In one preferred form, the decoding circuit determines one data bit value based on based on whether a paired sequence of pulses is in a present-then-absent order, and an opposite data bit value based on an absent-then-present order, in another, the decoding circuit determines a data bit value based on the order of the polarity of a biphasic pulse, in yet another, the decoding circuit determines a data bit value based on whether a biphasic pulse is relatively wide or narrow, and in still another form, the decoding circuit determines a data bit value based on a measure of relative amplitude of a biphasic In fact, the decoding circuit could determine data bit values based on a combination of modulations in said subthreshold pulses.

The useful information communicated can represent marker channel information, data representing physiologic data about a patient or information about a device sending the subthreshold communications from within a body.

The system operates via a method for communicating between an implantable medical device and an external device, starting with some data within an implantable medical device, sending a triggering signal to an implantable medical device, activating said implantable medical device in response to said triggering signal so as to encode and send a modulated set of subthreshold electrical pulses from said implantable device in accord with a protocol having for each data packet a header followed by substantive information, receiving the subthreshold pulses across a pair of electrodes on the surface of the body and decoding modulations of said subthreshold pulses so as to produce a data output representative of the data transmitted by the implantable medical device.

Preferably, the encoding further adds in error correcting code data to the modulated subthreshold pulses in each packet.

On the other side of the communications system is the implantable medical device which has a memory for storing data to be transmitted to an external device and a communication circuit for transmitting subthreshold signals representing data stored in said memory across electrodes external to but electrically connected to the communications circuit, wherein said communications circuit has a generating circuit for producing a biphasic pulse having a modulatable characteristic, said producing circuit adapted to configure each biphasic communications pulse in a pulse train in accord with a value represented by a modulation information signal, a conversion circuit for providing to said generating circuit said modulation information signal to control the modulation of said biphasic pulses, and a configuration circuit for translating data signal values from said memory into modulation signal values for sending said modulation values to said conversion circuit in a stream of values representative of an encoded translation of said data values in said memory. It should also have a trigger circuit for receiving a trigger signal from outside a body and for producing an internal trigger signal on such an occurrence, and an initiation circuit to receive said internal trigger signal from said trigger circuit and on such receipt to initiate program control of functioning of said generation, translation, and configuration circuits so as to send a stream of translated, converted and modulated biphasic communications pulses across said electrodes. In one embodiment, the present invention is a system that includes an implantable medical device having a can with surface electrodes positioned for contact with patient tissue. The system also includes a pair of stimulation electrodes for connection to patient tissue and a pulse generation circuit inside the can. The system further includes an electrode switching circuit that is coupled to the pulse generation circuit and delivers electrical stimulation pulses produced by the pulse generation circuit that are above a patient tissue stimulation threshold to the pair of stimulation electrodes as therapy to a patient. The electrode switching circuit also delivers subthreshold pulses produced by the pulse generation circuit to the can surface electrodes in a predetermined pattern of modulations constituting an encoded data signal that propagates as a signal transmission through the patient tissue. The system also includes a control circuit that is coupled to the pulse generation circuit and the electrode switching circuit, causes the pulse generation circuit to selectively generate the stimulation pulses and the subthreshold pulses, and causes the electrode switching circuit to selectively apply the selectively generated pulses to the pair of stimulation electrodes and the can surface electrodes. The system also includes a plurality of electrodes adapted to be electrically connected to a patient's skin to receive the subthreshold pulses transmitted through the patient tissue. In addition, the system includes an external device coupled to the skin electrodes to detect the encoded data signal.

Of course, any communications to the external device could be done so as to later be sent by the external device across a telephone or other communications network to a medical information group located at a distant receiver.

Numerous other features and advantages are described with reference to the following drawings.

DETAILED DESCRIPTION OF PREFERRED EMBODIMENTS

Figure 1:
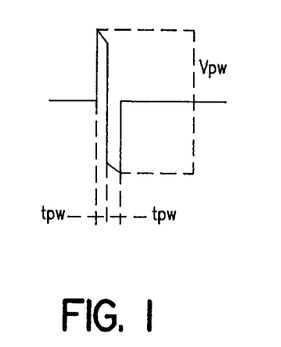
FIG. 1 is a graph of a generalized biphasic pulse for use with this invention.

The basic pulse waveform is shown in FIG. 1 by line 10. In general it can be described by an amplitude expressed in voltage ($V_{pw}$) and either side of the biphasic pulse can define a specific time period ($T_{pw}$). (For physiologic reasons, the net energy delivered to the muscle must be zero.) In order to code data using these pulses, characteristics of each individual pulse may be modulated, the relationship between pulses may be modulated, or some combination of techniques used. Each modulation technique can be used to include multiple bits per pulse to raise the transmission rate. Combining multiple techniques can additionally raise the information transfer rate.

Figure 4:
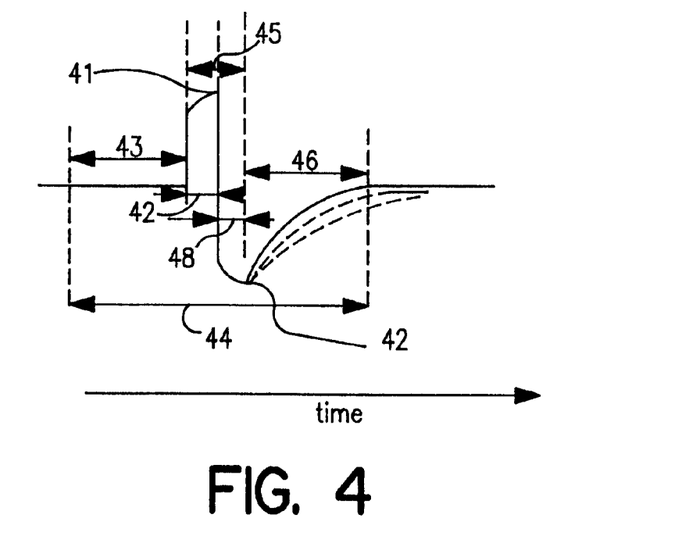
FIG. 4 is a graph of a preferred biphasic pulse for use with this invention.

FIG. 4 describes a single subthreshold waveform 40 having been positive peak at 41 and a negative peak at 42, and timing measurements described by arrows 43–48.

Figure 5:
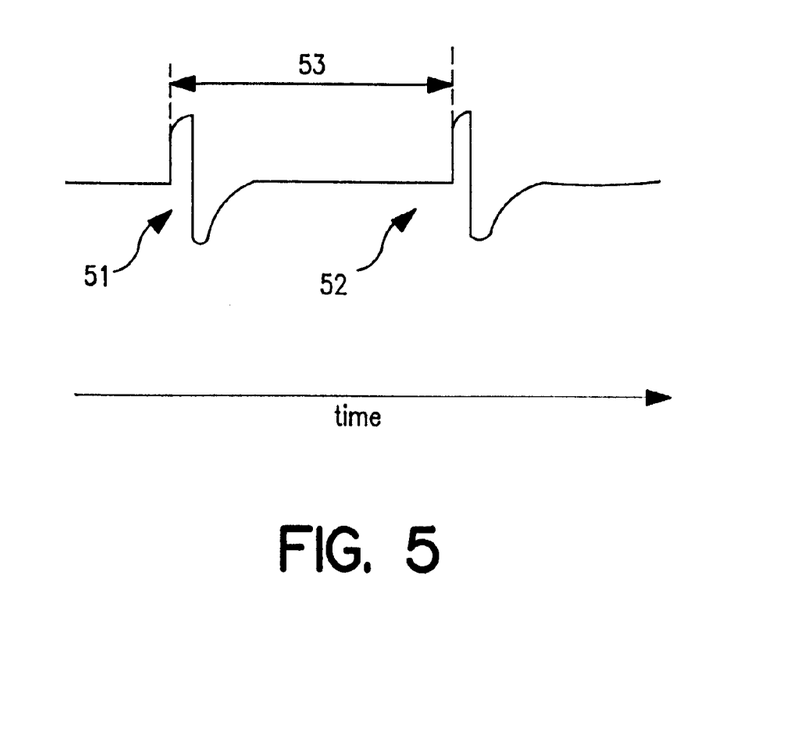
FIG. 5 is a graph of a pair of preferred biphasic pulses for use with this invention

FIG. 5 is being graph 50, of two adjacent pulses 51 and 52, having the same time measurement values on pulse 51 and additionally describes a new time parameter illustrated by arrow 53.

Figure 2:
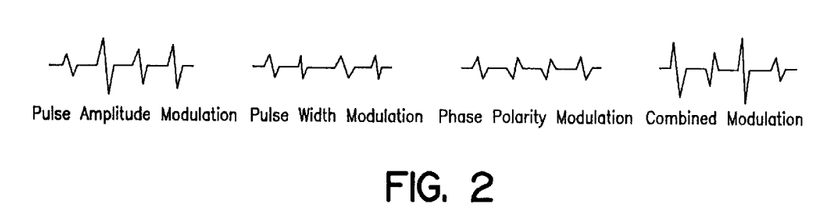
FIG. 2 is a graph of four broken segments showing pulse modulation features in accordance with preferred forms of this invention.

Individual pulses can vary by width ($T_{pw}$) or amplitude ($V_{pw}$). Additionally by choosing complementary pair electrode hardware (e.g. delivering the pulse, tip to can first and then can to tip in a pacemaker configuration), the polarity relationship of the pulse phases can be changed from positive/negative to negative/positive. Such variations as just described are illustrated in FIG. 2. Note on the figure the changes in height of the pulses on line 3, the width of the pulses on line 4, the change in the order or phase polarity on line 5 of the pulses, and the one combined form of amplitude, width, and polarity modulation in line 6. The interval between pulses can also be used to include data bits of information. The repetition rate (pulse frequency modulation) or missing pulse configuration in a constant rate pulse train (another form of pulse frequency modulation) may be used to encode information into the pulse stream of subthreshold pulses.

Also, missing pulse modulation is difficult to combine with the modulations illustrated in FIG. 2 since pulses would frequently be omitted in the pulse stream. This would make interpretation difficult. In general the specific technique or techniques must be decided by the user of this invention as a result of considering trade-offs between increasing data rate with more complex demodulation, lower cost external instruments, and achieving a specific level of reliability.

For the purpose of explanation, we describe a simple frequency pulse modulation scheme that is easily decoded and produced, employing a constant space between times for pulses to possibly occur and the absence or occurrence of a pulse during such times indicating a data "1" or "0". However we also describe how to enable numerous other modulation schemes which employ the available features of the subthreshold pulse we can deliver. One of ordinary skill in this art can employ the heuristic principles described with reference to the simple frequency modulation scheme we describe to the other forms of pulse modulation available without difficulty. The designer of a device in accord with this disclosure will have to consider that the more complex the modulation scheme employed, the more complex and expensive the receiver will probably have to be. Accordingly it is expected that the person of ordinary skill have some knowledge of the use of biopotential amplifiers.

Figure 6:
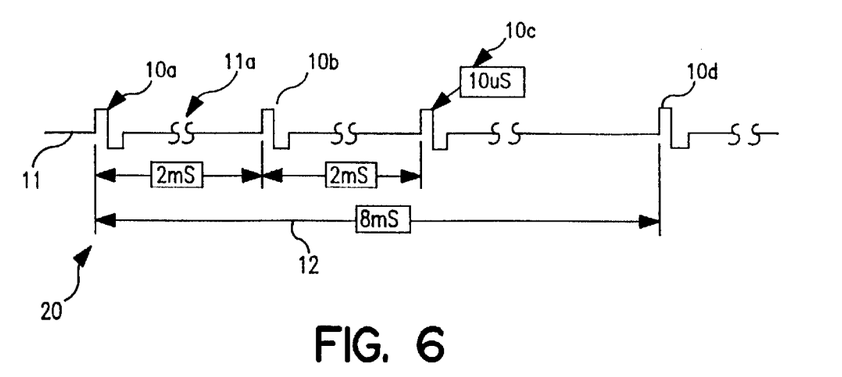
FIG. 6 is a graphic drawing of a pulse stream in accord with a preferred form of this invention.

FIG. 6 illustrates an 8 millisecond segment 20 of information under this simple modulation scheme. In this space of 8 mS, 5 pulses can be sent, but only 4 are, pulses 10a–d. (The segment may also be considered 10 mS long if you include the full time for the fifth pulse to end before the 6 the pulse may be allowed to occur). The time between each same sized and polarity simple biphasic subthreshold pulse is expected to be (for this modulation scheme) 2 mS. There is one space for a pulse missing between pulse 10c and 10d. Thus, the segment would be read, in its simplest form as a digital data stream of 11101. As is well known to those of ordinary skill in the communications art, this could be a part of a series of allowable pulse configurations, for example where only one "zero" is allowed and must be positioned in either the second or fourth position, thus yielding only three bits of information from a five pulse long code. Such pulse code schemes are used to enhance through redundancy the ability of a receiver to guess at the correct data where, for example one or another pulse might be lost in a noisy environment. We use checksum data for example, but other redundancies and well know schemes used for the same purposes should be considered to be within the ambit of this invention.

Figure 7:
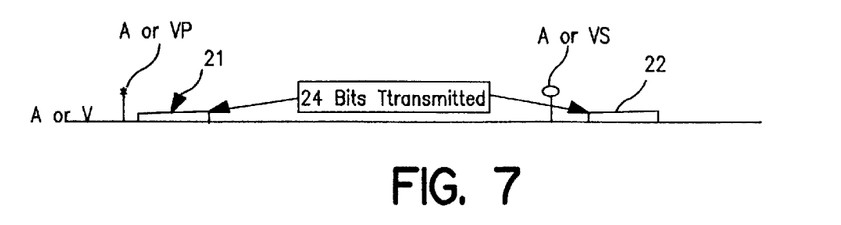
FIG. 7 is a graphic representation of a timing diagram with cardiac event features and time periods highlighted as features thereon.

Another preferentially designed feature is the limitation of transmission times to segments of time related to a sensed cardiac event or a pacing pulse. (Use of this feature is preferred especially where the receiver cannot distinguish communications pulses from physiologic signals very well, or more importantly, where there may be doubt about the inability of the communications pulses to trigger physiologic reaction in the patient's cells). FIG. 7 illustrates such a preferred embodiment. The segments such as segment 20 of FIG. 6 are limited in time to a period wherein the tissue is refractory to responding to stimulation after the delivery of a pulse (A or VP point on the line 25) or after an equal amount of time following a cardiac natural event (A or VS). These preferred transmission time periods are referenced with numerals 21 and 22.

Figure 8:
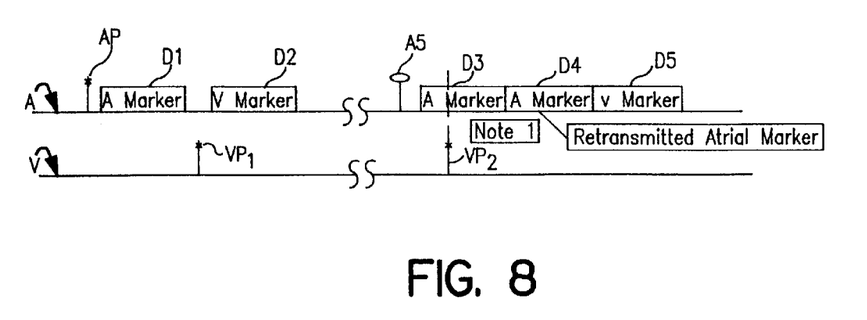
FIG. 8 is a graphic representation of a timing diagram like FIG. 7.

Referring to FIG. 8, there is a single channel transmission in the atrial channel having marker channel information in each transmission. The atrial channel is on line A and the ventricular channel is line V. In this illustrated scheme, a redundant transmission occurs after an event, here VP2, was triggered by the occurrence of an Atrial Sense event AS. Since it occurred in the transmission frame of the Amarker D3, the same Amarker data will be retransmitted.

Such periods are chosen to be set for the period of time the cardiac tissue is refractory to stimulation, thus even communication of subthreshold pulses near the stimulation threshold for the tissue will not cause a depolarization. These times of absolute tissue refractoriness are well known in the pacemaker art.

When used in this manner, simple but powerfully descriptive maker channel information can be transmitted. (The seminal disclosure regarding marker channel information generally is U.S. Pat. No. 4,374,382 issued to Markowitz and incorporated herein by this reference). Thus, for a 24 bit data stream in each space following a pacing pulse the available amount of information for transmission using our simple preferred scheme for modulation is $2_{24}$ messages. Thus, the receiving device could have a lookup table with $2_{24}$ entries, which could be used for transmitting that much information regarding the present state of the implanted device, it's history, the patient's physiological event history and in fact, any data usefully used outside the body where the implant resides. It is of course, important to recognize that with the inclusion of framing and error checking information as integral parts of the bit stream, substantially less than this amount of data will be available. Thus, the size of the table could be reduced to include spacer information, headers, or other redundancies to ensure correct receipt of the intended transmitted information, as might be designed into the table by one of ordinary skill. Or, the protocol information can be used by a preprocessing circuit or program to send the remaining substantive data to the table look-up circuit or program. The receiving device could use this information to print maker channel information on the moving electrocardiograph it is making, and/or store the information for later retrieval or transmission to a more empowered device where the information can be interpreted for diagnostic or research purposes.

In our preferred embodiment, we developed a specific integrated circuit for varying the parameters described across a range of values in a series of discrete steps. See Table 1 below for these values. A designer of systems employing this invention can make changes in these selections and ranges within the ambit of this invention so long as the changes continue to provide distinguishable features for the receiver and so long as the pulses are modulated to remain below the threshold which would adversely affect body tissue through electrical stimulation.

Just to detail the clear implications for data transmission again; with a simple modulation scheme as we are detailing here for a preferred form, for example, using a single binary modulation at 2 mS/pulse area, the data rate is about 50 bits per second; or using a similar single pulse modulation scheme such as phase polarity at 125 bits per second, thus the raw data or bit rate is limited to 125 bps. By using some of the independent modulation schemes described above, nine bits per pulse can easily be achieved with a resulting raw data rate of 1125 bps. However, using such high data rates requires a more sophisticated reading device to parse the information from the analog encoding of small power signals, and since for the present moment, price is the main consideration, the simpler modulation schemes are preferred.

Since this data transmission scheme is for transmitting data from between implanted device within a patient's body and an inexpensive external device similar to an electrocardiogram receiver/recording device, some type of redundant transmission information is useful to ensure good transmission of data through noisy environments and less than ideal conditions. Redundancy is also important because there is little or no opportunity to inform the implant that its data is not understood, even if the inexpensive receiver could determine that the data is not good by itself. Multiple transmissions of the same data, and/or various forms of error correction are both classes of useable redundancy that may be employed for this. In one preferred embodiment we send a message having an error correcting code incorporated into the message and use a decoding circuit to correct any errors located in the message. Depending on the complexity of this added redundancy, which will need to be included, the amount of data that can be sent in a given time period will be reduced by from about 5 to 70%.

In another preferred embodiment, we transmit data continuously once the transmission is activated without regard to refractory periods since the size of the pulses is too small to stimulate the tissue response. In this preferred embodiment, much more data can be transmitted in the same period of time since we don't have to wait for refractory periods.

Specifically, in our preferred example embodiment, information is transmitted as words that are 24 bits in length. We could design this in numerous ways, but for marker channel information a word of approximately this length or shorter should be used if transmission time is limited to refractory cardiac times, and is using something close in date rate to the example modulation scheme. Our preferred marker channel words are 21 bits in length. A word can represent data file header, data file segments, or marker channel information. For unipolar lead configuration one word is transmitted per pacing cycle. For bipolar lead configuration up to four words are transmitted per pacing cycle. Marker channel information is transmitted with one word per pace or sense event. All bits within a word need to be transmitted without interruption. If the transmission of a word is interrupted the entire word must be retransmitted at the next available opportunity. A preferred data structure for the transmitted word is as shown.

It should be noted that where the implanted device has no concern about the potential to stimulate tissue, say for example, because it is merely a subcutaneous implant monitoring a local physiologic condition incapable of sending large stimulation pulses, than much longer/shorter or just different data structures could be used, as will by now be apparent to the reader. Additionally, the localization of the external electrodes near the subcutaneous device would obviate any concern about isolating the communication pulses from physiologically produced electric signals.

| Data Bit | Data File Header | Notes |
|---|---|---|
| D0, D1 | $11_2$ | Used for clock synchronization. D0 is first bit of word |
| D2–D6 | $00001_2$ | Indicates that this is a data file header |
| D7–D8 | $00_2$ to $11_2$ | Used to identify up to 30 data file segments as a group. |
| D9–D13 | $00000_2$ to $11111_2$ | Indicates the number of data file segments to be transmitted in a group. |
| D14 | Complete | Transmission complete indicator, 1 indicates that this is the last group to be transmitted. |
| D15–D18 | $00000_2$ to $11111_2$ | Unassigned data file header bits. |
| D19–D23 | ECC | Error detection and correction information. |

-continued

| Data Bit | Data File Segment | Notes |
|---|---|---|
| D0, D1 | $11_2$ | Used for clock synchronization. |
| D2–D6 | $00010_2$ to $11111_2$ | Used to order data file segments for reconstruction of data file. 30 segments can be ordered. |
| D7–D18 | Data (12 bits) | Data field for a data file segment |
| D19–D23 | ECC | Error detection and correction information. |

| Data Bit | Marker Channel | Notes |
|---|---|---|
| D0, D1 | $11_2$ | Used for clock synchronization. |
| D2–D6 | $00000_2$ | Indicates that this is marker channel information |
| D7 | Lead | 0=Atrial lead, 1=Ventricular lead |
| D8 | Event | 0=Sense event, 1=Pace event |
| D9 | Sense type | 0=Non refractory sense, 1=Refractory sense |
| D10–D15 | Correction | The number of 10 ms10mS periods prior to the first bit of this frame that the marker event occurred. Result rounded to the nearest 10 msmS. |
| D16–D20 | ECC | Error detection and correction information. |

In one example embodiment that limits transmission to refractory periods but includes marker channel information, data files consist of a data header file and up to 30 data file segments. Such segments can be broken across the refractory periods used in the marker channel transmission times if desired, but this may result in a slower transmission of large amounts of data. On the other hand, by only transmitting in the refractory period, the implanted device is assured of not capturing the cardiac tissue. All information is transmitted twice to allow for the recovery of missed information. If the reading device is expecting the information after the pace (or sensed event) pulse, there is no need for a header. Similarly, marker channel information does not require a header. Marker channel transmission occurs once per event. Incorrect information that can not be corrected with the checksum information will be discarded by the receiver. The data file is constructed as shown:

| File Transmitted | Pace Event | Cumulative Transmission Time at 85 BPM |
|---|---|---|
| Unipolar leads | | |
| Data header file (group 0) | 1 | |
| Data header file (group 0) | 2 | |
| Data file segment (0) | 3 | |
| Data file segment(1) | 4 | |
| Data file segment(n), n ≦ 29 | 32 for n=29 | 23 seconds |
| Data file segment (0) | 33 | |
| Data file segment(n), n ≦ 29 | 64 for n=29 | 45 Seconds |
| Bipolar leads (Example shows two groups transmitted) | | |
| Data header file (group 0) (Transmission complete bit = 0) | 1 | |
| Data header file (group 0) | 1 | |
| Data file segment (0) | 1 | |
| Data file segment(1) | 1 | |
| Data file segment(n), n ≦ 29 | 8 for n=29 | 5.6 seconds |
| Data file segment (0) | | |
| Data file segment(n), n ≦ 29 | 16 for n=29 | 11.2 Seconds |
| Data header file (group 1) (Transmission complete bit = 1) | | |
| Data header file (group 1) | | |
| Data file segment (0) | | |

-continued

| File Transmitted | Pace Event | Cumulative Transmission Time at 85 BPM |
|---|---|---|
| Data file segment(n), n ≦ 29 | | |
| Data file segment (0) | | |
| Data file segment(n), n ≦ 29 | 32 for n=29 | 22.4 Seconds |

Figure 10:
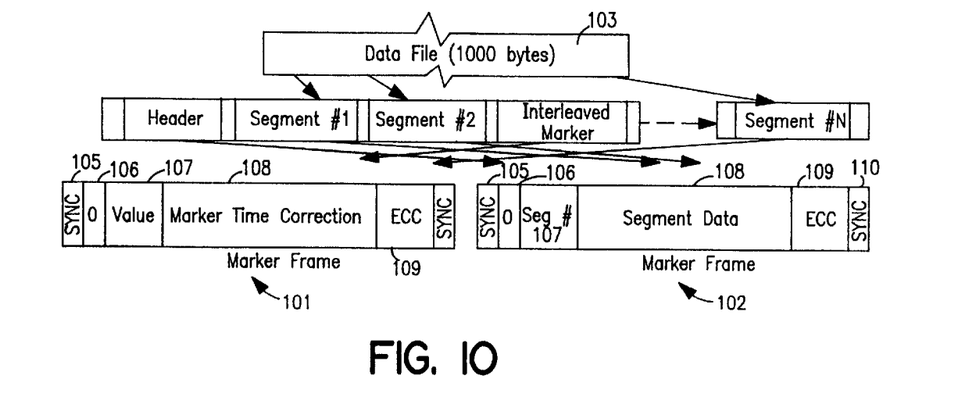
FIG. 10 is a block diagram representation of a protocol.

Additionally one may wish to employ a more detailed protocol. An example protocol for data communications is described with respect to FIG. 10 wherein a Marker Frame 101 and a Data Frame 102 structure can coexist in a single transmission. Here the data file bit stream 103 is broken across the two frames 101 and 102 and it resides in chunks of the segment data within the protocol marked Segment #1-N. A synchronization portion 105, a marker space which is zero in one frame and one in the next to distinguish one frame form another 106, segment number or marker type 107 marker time correction data 108 error correcting code 109, and final synchronization space 110, transmitted in the order shown, make up the overall protocol, allowing for easy decoding by a compatible reading device. In a segment having other data than marker data such as frame 102, the segment 108 contains the data. One of ordinary skill in the data communications art will be able to produce innumerable protocol arrangements and the specifics are best left to the designer of the specific devices. Error correcting codes are well known in that field as well. See for example, *Error Control Coding: Fundamentals and Applications* by Lin and Costello, Prentice Hall, Inc., Englewood Cliffs, N.J., Copr. 1983, and *Error Correcting Codes* by Peterson and Weldon, 2nd Edition, MIT Press, Boston, Copr. 1972.

Figure 3:
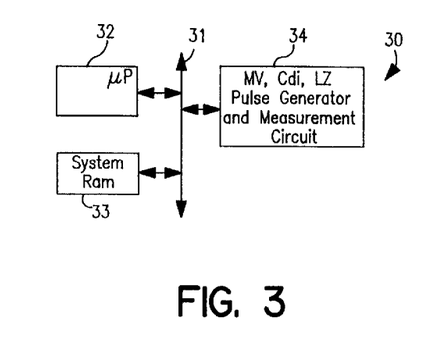
FIG. 3 is a heuristic block diagram.

The preferred circuitry is described in overview with reference to FIG. 3. A bus 31 connects a microprocessor 32 with the memory 33 and the pulse generator and measurement circuit 34 which develops the subthreshold communications pulses (as it also can develop other subthreshold pulses for purposes such as determining minute ventilation through impedance measurements as was described in U.S. Pat. No. 4,702,253 issued to Napholtz, among others. Such pulses can have other alternative uses as well which may be employed by the same circuitry for generating these pulses any time they are not being used for communications as they are for this invention). A microprocessor or other control circuitry 32 formats a set of register values to be sent to the excitation control register. These register values set the parameters of each individual pulse and its timing to include the desired data values and redundancy. To start communication, the microprocessor writes the first value to the control register under firmware control. Subsequent values are automatically transferred from memory to the control register by either the microprocessor or a the direct memory access (DMA) controller circuit in the microprocessor. A program in memory may control the processor circuit 32 to encode the data sent with the appropriate conversions to the transmission code and include any protocol features that may be required. Microprocessor and program control are the most flexible way to set this operation up, however one could use fixed analog circuitry to avoid use of registers and other memory devices if desired, but that would not be preferred.

Figure 11:
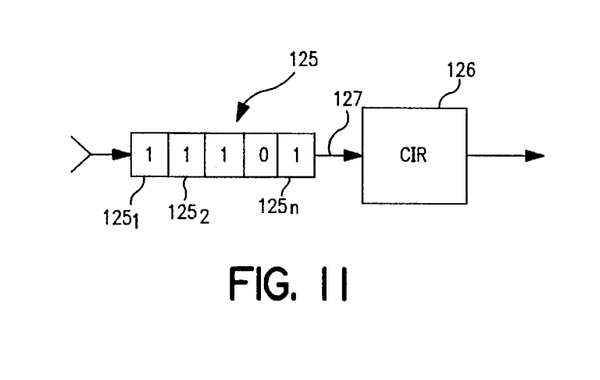
FIG. 11 is a block circuit diagram.

An example preferred excitation control register 125 is shown in FIG. 11. As it is well known how to convert values in a register to signal values to modulate a waveform no detailed description is provided here. It is sufficient to say that a larger number of elements ($125_{1 \ldots n}$) provides more flexibility in range between the two polar values of a given pulse modulation characteristic (such as amplitude or pulse width). But since in our preferred embodiment we only determine whether a pulse or non pulse condition will occur at the time for a next pulse during a communication, the flexibility provided by such a register is surplussage for this simple embodiment. If however one prefers to enable more forms of modulation, the diagram of FIG. 11 should be referenced. There, the value in register 125 would program an output circuit 126 to produce the pulse modulated for the characteristics defined by the data in the register 125.

Figure 9A:
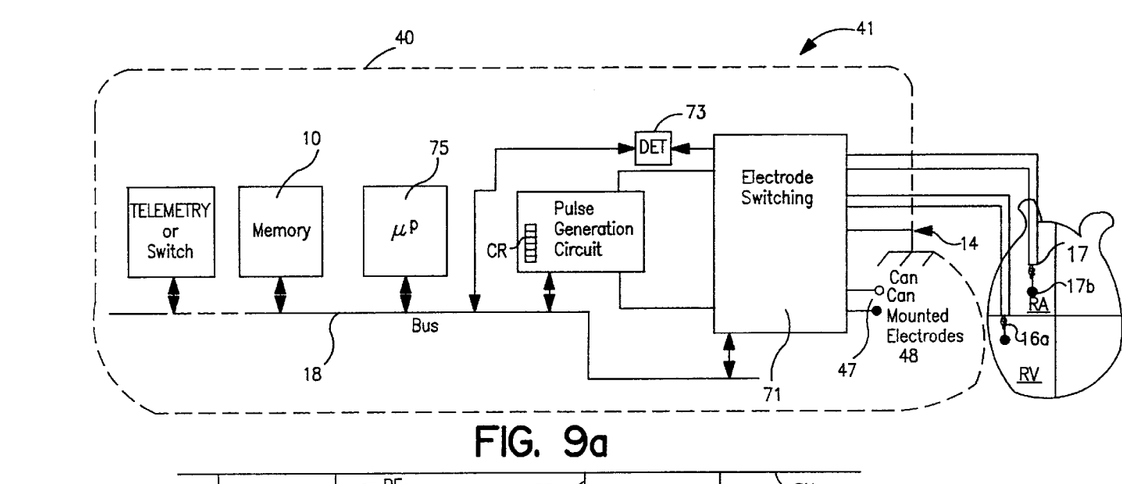
FIG. 9a is a simplified block diagram representing the features an implanted device may have in a preferred form of the invention.

FIG. 9a represents the shell of the implanted device in dotted line 40, here having two surface electrodes 47 and 48, electrically isolated from each other. There may also be electrodes such as an indifferent electrode employing the exterior metal can or housing 14, and electrodes 16a 16b 17a and 17b on leads located so as to provide stimulation within specific tissues, as illustrated here, in a heart right atrium RA and right ventricle RV. These devices could be pacemakers, cardioverter/defibrillators, drug pumps, or any implanted device which can generate subthreshold pulses for communication in accord with this description. The form of the implanted device is relevant to the choice of modulation and data transmission schemes as has been explained throughout this document. For example, a simple two to four electrode subcutaneous electrocardiogram recording device has no chance of accidentally causing physiologic changes in tissue during use of the communications pulses, so continuous rather than only refractory time communication would be preferred. The systems with more electrode choices may be used to enhance the signal received by the reading device through experiment and the preferred transmission set of electrodes may be fixed at the time of implant.

In FIG. 9a, only the relevant features of a typical implanted device which could be used with this invention are shown. The pulse generator circuit 74 creates the waveform pulse and sequence of pulses in accord with parameters written by the microprocessor 75 under program control to the control register CR of circuit 74. The Microprocessor 74 may transfer these parameters through a DMA circuit or across bus 18. The output of circuit 74 is applied to the electrode switching circuit 71 in accord with the preferred sending path to the selected electrode pair. The configuration of the switches in circuit 71 is determined by values in its control register (not shown) which are in turn selected by the microprocessor under program control. The data communicated will generally reside in a specific area of the memory circuit 10, having been stored there by the implanted device during its normal operation for this purpose. The application of the waveform pulse across a pair of electrodes causes a current to flow and be detectable by an external reading device via electrodes affixed to the skin of a patient. The initiation of a communications session as just described is preferably performed by the activation of some internal switch such as a reed switch or Hall-effect sensor by a magnet placed near the implanted device, or by some kind of telemetered wakeup signal generated by a programmer or a simple activator device capable of transmitting a simple activation sequence. this function is illustrated here by the use of a "telemetry" block in dotted line within the shell 40 of device 41.

Figure 9B:
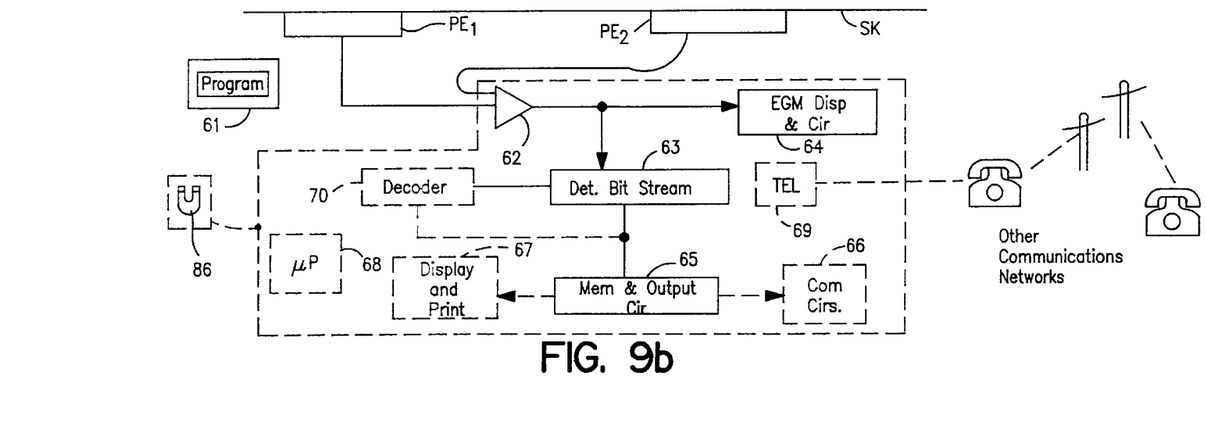
FIG. 9b is a simplified block diagram representing the exterior (outside of the patient) device as would be used with a preferred form of this invention.

FIG. 9b. illustrates an external reading device 60 connected electrically to a patient's skin SK by electrodes PE1 and PE2. The signals received by these electrodes (which could be any combination of known electrocardiogram type electrodes) is fed into a receiving sense amplifier circuit 62, and commonly will produce an analog display of an electrocardiogram 64 which represents the varying signal value found between any two of the leads on the patient's body. Additionally, the input signal is sent to a decoding circuit 63 that detects the bit stream in any of the manners described above, depending on the design of the reading device 60. The data from that stream is fed to a memory and output management circuit 65 for storage and use through communications circuits 66 or by adding to the display or printing an additional display via circuits 67, if desired. Additionally the data may be received in a coded format that requires a decoder circuit to do error correcting and accommodation to redundancies or intradata modulation techniques. Further a microprocessor circuit 68 may have a program that operates on the received data to perform diagnostic or other reporting functions, and a telephonic transmission or other transmission circuit may send the relevant data received and/or digested by the programs to some other devices for further use. Commonly a programmer device 61 will be a receiving device for such information and may perform additional operations on the data. The trigger for the transmission by the device 40 may be from an attached or separate trigger device 86, here a simple magnet, which acts upon the circuit 77 in an appropriate manner to the circuit 77 design. A separate programmer device 61 could also provide the trigger to start the transmission by the implant 40.

What is claimed is:

1. A system, comprising:

an implantable medical device having a can with surface electrodes positioned for contact with patient tissue;

a pair of stimulation electrodes for connection to patient tissue;

a pulse generation circuit inside the can;

an electrode switching circuit coupled to the pulse generation circuit and delivering electrical stimulation pulses produced by the pulse generation circuit that are above a patient tissue stimulation threshold to the pair of stimulation electrodes as therapy to a patient and delivering subthreshold pulses produced by the pulse generation circuit to the can surface electrodes in a predetermined pattern of modulations constituting an encoded data signal that propagates as a signal transmission through the patient tissue;

a control circuit coupled to the pulse generation circuit and the electrode switching circuit to cause the pulse generation circuit to selectively generate the stimulation pulses and the subthreshold pulses and to cause the electrode switching circuit to selectively apply the selectively generated pulses to the pair of stimulation electrodes and the can surface electrodes;

a plurality of electrodes adapted to be electrically connected to a patient's skin to receive the subthreshold pulses transmitted through the patient tissue; and an external device coupled to the skin electrodes to detect the encoded data signal.

2. The communications system of claim 1, wherein the control circuit includes a microprocessor.

3. The communications system of claim 1, wherein the pulse generation circuit modulates the second electrical pulses using a mechanism selected from the group consisting of frequency modulation, amplitude modulation, pulse train modulation, pulse width modulation, and pulse polarity modulation.

* * * * *